US006695785B2

(12) United States Patent
Brisken et al.

(10) Patent No.: US 6,695,785 B2
(45) Date of Patent: Feb. 24, 2004

(54) CATHETER INCLUDING ULTRASOUND TRANSDUCER WITH EMISSIONS ATTENUATION (75) Inventors: Axel F. Brisken, Fremont, CA (US); N. Parker Willis, Atherton, CA (US)

(73) Assignee: Cardiac Pathways Corporation, Sunnyvale, CA (US)

( * ) Notice: Subject to any disclaimer, the term of this patent is extended or adjusted under 35 U.S.C. 154(b) by 0 days.

(21) Appl. No.: 09/934,439

(22) Filed: Aug. 21, 2001

(65) Prior Publication Data

US 2002/0099292 A1 Jul. 25, 2002

Related U.S. Application Data (62) Division of application No. 09/192,763, filed on Nov. 16, 1998, now Pat. No. 6,277,077.

(51) Int. Cl.[7] .................................................. A61B 8/12
(52) U.S. Cl. ....................................................... 600/459
(58) Field of Search ................................. 600/459–472; 310/334–362; 29/25.35; 264/165, 176.1

(56) References Cited

U.S. PATENT DOCUMENTS

| 4,382,201 | A | | 5/1983 | Trzaskos |
| 5,076,278 | A | * | 12/1991 | Vilkomerson et al. ... 73/861.25 |
| 5,389,848 | A | | 2/1995 | Trzaskos |
| 5,406,951 | A | * | 4/1995 | ten Hoff et al. ............ 600/446 |
| 5,588,432 | A | | 12/1996 | Crowley |
| 5,844,140 | A | | 12/1998 | Seale |
| 5,848,969 | A | | 12/1998 | Panescu et al. |
| 6,019,725 | A | | 2/2000 | Vesely et al. |

FOREIGN PATENT DOCUMENTS

| WO | WO 98/08440 | * | 3/1998 |

OTHER PUBLICATIONS

Ratcliff et al. "Use of Sonomicrometry and Multidimensional Scaling to Determine the Three–Dimensional Coordinates of Multiple Cardiac Location: Feasibility and Initial Implemention", IEEE, *Transactions on Biomedical Engineering*, vol. 42, No. 6.

Gubbels, Andrew "Sonomicrometer Enhancement –Implementing 16–Bit Counters into EPLDs", The University of Western Ontario, Faculty of Engineering Science, E.S. 400–Project Report; Mar. 25, 1993, pp. 4 and 5.

Van Trigt, III, Peter et al. "An Improved Transducer for Measurement of Cardiac Dimensions with Sonomicrometry", The American Physiological Society (1981), pp. H664–H668.

* cited by examiner

Primary Examiner—Francis J. Jaworski
(74) Attorney, Agent, or Firm—Bingham McCutchen LLP (57) ABSTRACT A catheter including an elongated body member, an ultrasound transducer located on the elongated body member, and dampening means for forming an ultrasound dampening region adjacent to a portion of the ultrasound transducer, is disclosed. The ultrasound transducer is configured to transmit or receive an ultrasound signal. The ultrasound dampening region is configured to improve uniformity of said ultrasound signal in three-dimensional space. Preferably, the dampening means includes air or a material containing air.

33 Claims, 10 Drawing Sheets

CATHETER INCLUDING ULTRASOUND TRANSDUCER WITH EMISSIONS ATTENUATION

RELATED APPLICATIONS

This application is a divisional application of U.S. application Ser. No. 09/192,763 filed Nov. 16, 1998, now U.S. Pat. No. 6,277,077.

BACKGROUND OF THE INVENTION

1. Field of the Invention

The present invention relates to ultrasound transducers. In particular, the invention relates to ultrasound transducers mounted on catheters that include ultrasound dampening regions to improve the performance thereof.

2. Description of the Related Art

For certain types of minimally invasive medical procedures, endoscopic visualization of the treatment site within the body is unavailable or does not assist the clinician in guiding the needed medical devices to the treatment site.

Examples of such procedures are those used to diagnose and treat supra-ventricular tachycardia (SVT), atrial fibrillation (AF), atrial flutter (AFL) and ventricular tachycardia (VT). SVT, AFL, AF and VT are conditions in the heart which cause abnormal electrical signals to be generated, causing irregular beating of the heart.

A procedure for diagnosing and treating SVT or VT involves measuring the electrical activity of the heart using an electrophysiology (EP) catheter introduced into the heart via the patient's vasculature. The catheter carries mapping electrodes which are positioned within the heart and used to measure electrical activity. The position of the catheter within the heart is ascertained using fluoroscopic images. The mapping electrodes measure the electrical activity of the heart at the position of the catheter. A map is created by correlating locations in the heart determined by viewing the position of the catheter with the fluoroscope. The physician uses the map to identify the region of the endocardium which he believes to be the source of the abnormal electrical activity. An ablation catheter is then inserted through the patient's vasculature and into the heart where it is used to ablate the region identified by the physician.

To treat AF, an ablation catheter is maneuvered into the right or left atrium where it is used to create elongated ablation lesions in the heart.

An improvement over fluoroscopy is a display system using a fixed coordinate system for determining the relative locations of medical devices within the body. Such a display system using a fixed coordinate system can avoid the tracking errors inherent in fluoroscopic imaging that can make it difficult to guide medical devices to the desired locations within the body. Ultrasound can be used to track medical devices relative to a fixed internal coordinate system. Such an ultrasound tracking system uses at least four ultrasound transducers.

An ultrasound tracking system can be based on the time difference measured from the time an ultrasound pulse is transmitted by one transducer to the time it is received by another transducer. Given the velocity of sound in tissue and blood of approximately 1570 m/sec, the distance between the transmitter and receiver can be calculated. This process of distance measurement with sound is called sonomicrometry. Distance measurements between multiple transducers are used to triangulate the positions of the transducers in a three-dimensional coordinate system. A minimum of four transducers create a three-dimensional coordinate system, with three transducers defining a plane and the fourth defining a position above or below the plane. Additional transducers may be used for redundancy. Once the coordinate system is established, additional transducers on medical devices may be used to calculate the locations of the devices relative to the coordinate system.

Figure 1:
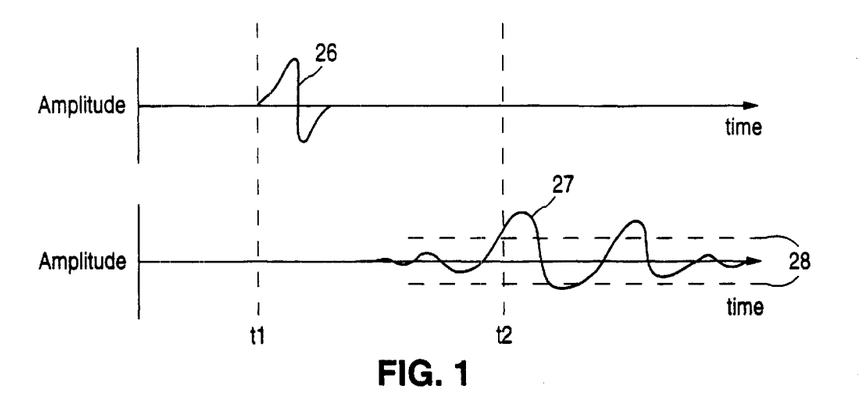
FIG. 1 is a graph of amplitude versus time for transmitted and received waveforms.

FIG. 1 shows an example of transmit and receive waveforms for a typical sonomicrometry procedure. Transmission waveform 26 is a pulse initiated at time t1 by a transmitting transducer. Reception waveform 27 corresponds to the voltage generated by a receiving transducer that intercepts the transmit pulse. The time t2 is the time at which the reception waveform crosses a detection threshold 28. The time difference between t1 and t2 may then be used to calculate the distance between the transmitter and the receiver.

The detection threshold 28 is needed to filter out detected signals that are too small to have been generated by a measurement pulse. Such signals could result from crosstalk with signals on nearby wires or from random noise.

For optimal performance of a sonomicrometer system, transducers should exhibit fully isotropic operation, that is, the same transmit or receive (or both) generation or detection sensitivity in all directions. Isotropic operation allows measurement of the same distance amount regardless of the orientation of the transducers. Accurate distance measurement is desirable for measurements within the human body, especially within the heart or other vital organs, both for accurate placement of the sensing devices and for accurate location of areas for monitoring or surgery.

Sonometrics Corp. of London, Ontario, Canada has developed a sonomicrometer system based on a family of small transducers which might be sewn onto living tissue. These transducers typically consist of either small, flat squares of piezoelectric ceramic 30 (FIG. 2) in a spherical bead of epoxy (not shown) or small cylinders of piezoelectric ceramic 34 (FIG. 3) in a spherical bead of epoxy (not shown).

Figures 2, 3:
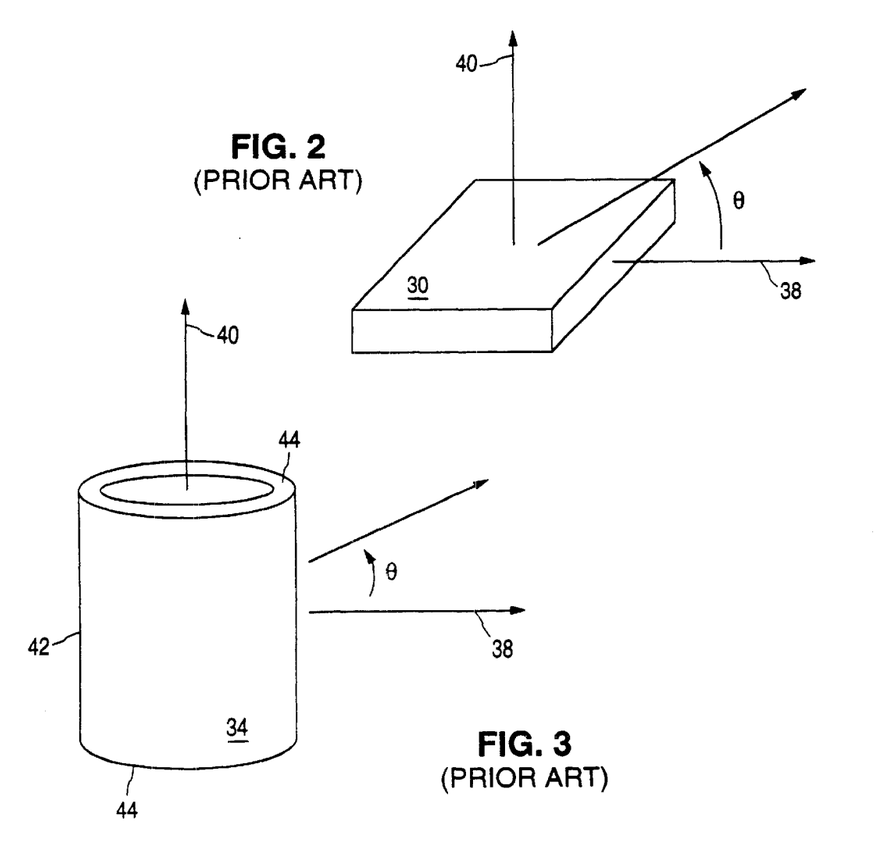
FIG. 2 is an elevation view of an existing rectangular transducer.
FIG. 3 is an elevation view of an existing cylindrical transducer taken on the longitudinal axis of the cylinder.

Piezoelectric ceramics convert electrical energy into vibrational energy, and vice versa. The vibration results from the piezoelectric ceramic expanding in one direction, which causes it to contract in another direction. For the square transducer 30, expansion by the top and bottom (thickness) causes the sides to contract. For the cylindrical transducer 34, expansion by the top and bottom (length) causes the thickness and the circumference to contract. Each direction of expansion/contraction is termed a vibrational mode.

The expansion and contraction causes an ultrasound signal to be emitted from each surface of the transducer when transmitting. Similarly, a received ultrasound signal causes a receiving transducer to expand and contract, generating electricity.

The epoxy bead serves as a lens to focus the ultrasound signal.

The frequency of expansion and contraction is determined by the size of the transducer. The speed of sound in the piezoelectric ceramic is about 4000 m/sec. This speed is equal to the wavelength times the frequency, and the wavelength is twice the direction of expansion/contraction. For example, for the square transducer 30, a length and width d of 0.052 inches relate to a frequency of 1.5 MHz. For the cylindrical transducer 34, the wavelength of the circumferential vibration is the average circumference, and the wavelength of the length vibration is twice the length, so a length of 0.052 inches and a circumference of 0.105 inches relate to a frequency of 1.5 MHz.

Line 40 in FIGS. 2 and 3 passes through the center of the transducer in a direction parallel to a longitudinal axis of a catheter (not shown) on which either of the transducers 30 or 34 may be mounted. Line 38 indicates a direction perpendicular to line 40, where line 38 passes through the center of the transducer. The angle $\Theta$ denotes the angle from line 38 in the direction of line 40.

Unfortunately, the transducers shown in FIGS. 2 and 3 are anisotropic because the physical geometry of the transducer contributes to the radiation emitted and received. For example, referring to FIG. 3, line 38 lies in a radial plane perpendicular to line 40 through the center of transducer 34. The cylindrical symmetry of transducer 34 suggests that the emissions or receptions in this plane would also be symmetric. However, for measurements made at an angle $\Theta$ as the angle approaches line 40 (an angle of 90 degrees), defining a longitudinal plane through the center of the cylinder, anisotropy in emissions results as the radiation shifts from emission off the cylindrical side to emission off the flat end 44 of the transducer. Similarly, referring to FIG. 2, anisotropy results from interference between the sides and the top.

Furthermore, anisotropy results from the physical dimensions of a receiving transducer at the same angles. This is because reception is symmetric to transmission For example, if an ideal emission source is moved around a stationary receiving transducer having a given geometric shape, this results in the same received waveform as when an ideal receiver is moved around a stationary transmitting transducer having the same geometric shape.

Measurements of the anisotropy of the devices shown in FIGS. 2 and 3 were on the order of 10 to 20 dB. Such anisotropy is undesirable because it disrupts accurate measurement of distances. For example, for a given distance d, measuring the distance between two transducers with isotropic radiation patterns will produce the same result regardless of the angular relationship between the two transducers. However, prior art transducers have anisotropic radiation patterns due to interference produced by emissions off the different surfaces. Such interference produces peaks and valleys in the radiated signal that vary based on the angle. Such peaks and valleys can occur at a time corresponding to the actual distance d, which causes the measured distance to vary because the wave may not be detected until after the interference minimum has passed. Such variation can be especially undesirable when performing the medical procedures described above, when accurate distance measurement is critical.

Figure 4:
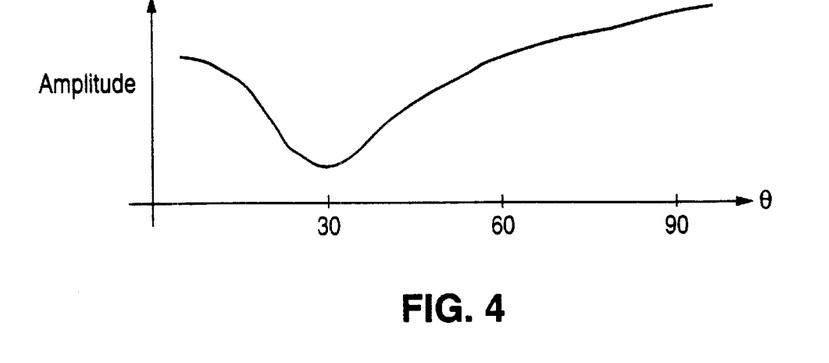
FIG. 4 is a graph of amplitude versus angle for the transducer of FIG. 3.

FIG. 4 illustrates the experimental results from catheters comprising small cylinders of piezoelectric ceramic around the catheter body. As can be seen, the amplitude of the signal (either transmitted or received) varies significantly with the angle $\Theta$. Similar irregular results were observed with and without a spherical bead of epoxy around the ceramic. Furthermore, these devices typically would exhibit phase reversals in their response at a $\Theta$ of about 30 degrees, this effect being due to a switch from emission off the cylindrical surface 42 of the ceramic to emission off the ends 44 of the cylinder (see FIG. 3). Emission off the ends 44 is 180 degrees out of phase with emission off the surface 42 because one expands while the other contracts, causing interference. These responses were considered unacceptable.

Figure 5:
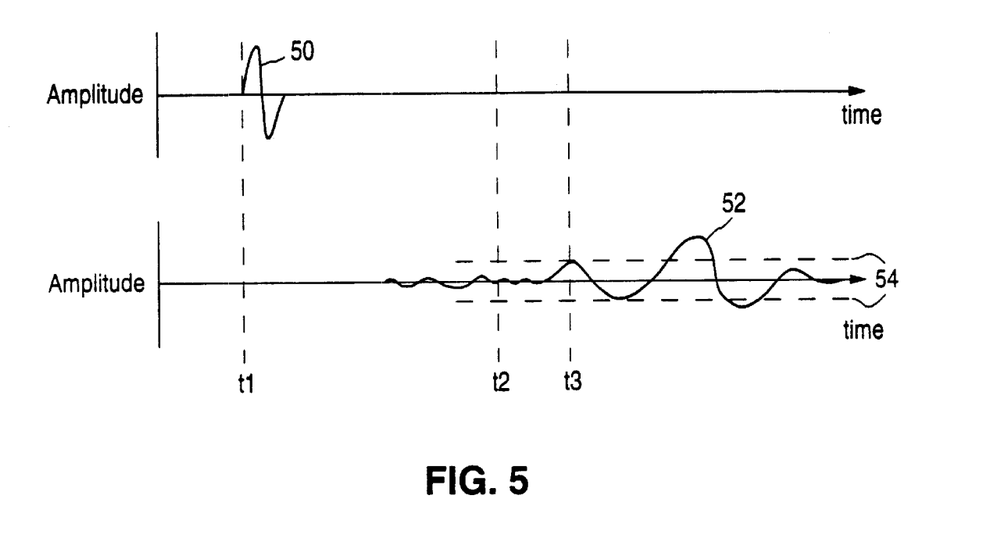
FIG. 5 is a graph of amplitude versus time for transmitted and received waveforms.

FIG. 5 illustrates exemplary waveforms showing how the interference from anisotropic radiation may result in distance measurement variations. Transmitted waveform 50 is pulsed at time t1. Received waveform 52 rises above the detection threshold 54 at time t3. The actual time that the wave should be received is at time t2 (compare with FIG. 1). Before time t2 the wave looks like it is about to be detected, but the anisotropy results in destructive interference between time t2 and time t3. Thus, the distance measurement of the wave in FIG. 5 will be longer than the actual distance. Thus, anisotropy causes the distance measurement to vary based on the relative angle between the transmitter and the receiver.

Figure 6A:
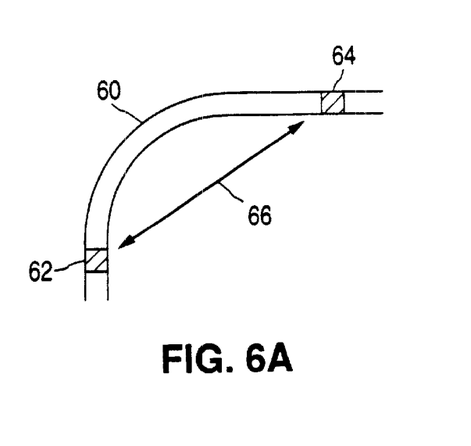
FIGS. 6A and 6B are cross-sectional views of a catheter taken on the longitudinal axis of the catheter.
Figure 6B:
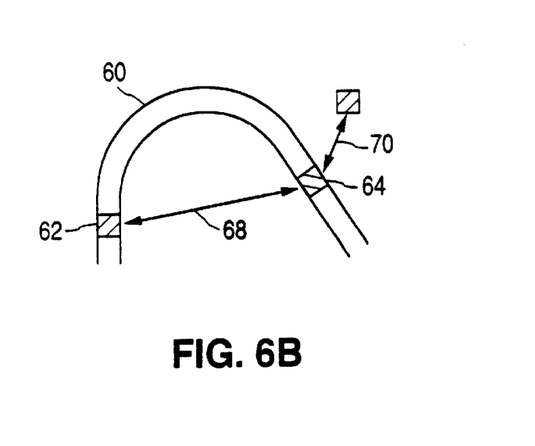

FIGS. 6A and 6B show a second problem that results when a catheter 60 has both a transmitting transducer 62 and a receiving transducer 64. FIG. 6A shows that desirably, a measurement pulse generated by transmitting transducer 62 should be received by receiving transducer 64 at a time corresponding to the distance 66. However, due to the higher velocity of sound in the catheter materials than in the surrounding blood and tissues, the pulse may propagate more rapidly along the catheter body than through the surrounding blood and tissues. In such a situation the distance measured, signified by the numeral 68 in FIG. 6B, will be shorter than the actual distance. When distance 68 is used to triangulate the position of transducer 64, an error 70 results.

In accordance with the subject invention, the angular transmission and detection response of a transducer assembly can be improved if the geometry and structure of the device are carefully considered. The present invention achieves this result by employing ultrasound dampening regions adjacent to the transducers to produce more isotropic transmission and reception.

Sonic energy does not propagate in a vacuum. Ultrasonic energy does not propagate well in air nor do piezoelectric transducers couple energy effectively into air, especially at frequencies up to and beyond 1 MHz. Consequently an ultrasound dampening region including air or a vacuum is proposed to inhibit emission and reception from selected surfaces of the transducer.

SUMMARY OF THE INVENTION

According to one embodiment, a catheter according to the present invention includes an elongated body member, an ultrasound transducer located on the elongated body member, and dampening means for forming an ultrasound dampening region adjacent to a portion of the ultrasound transducer. The ultrasound transducer is configured to transmit or to receive an ultrasound signal. The ultrasound dampening region is configured to improve uniformity of communication of the ultrasound signal in three-dimensional space.

According to another embodiment, a catheter according to the present invention includes an elongated body member, a plurality of ultrasound transducers located on the elongated body member, first dampening means for forming an ultrasound dampening region adjacent to a portion of the ultrasound transducer, and second dampening means for modifying a conducted ultrasound signal conducted by the elongated body member to inhibit detection thereof. The plurality of ultrasound transducers are configured to transmit and to receive a plurality of ultrasound signals. The ultrasound dampening region is configured to improve uniformity of corresponding communicated ultrasound signals in three-dimensional space. The second dampening means is located between one of the plurality of ultrasound transducers that sends the communicated ultrasound signals and another that receives the communicated ultrasound signals.

According to yet another embodiment, an ultrasound transducer assembly according to the present invention includes an ultrasound transducer and dampening means for forming an ultrasound dampening region adjacent to a portion of the ultrasound transducer. The ultrasound transducer is configured to transmit or to receive an ultrasound signal. The ultrasound dampening region is configured to improve uniformity of communication of the ultrasound signal in three-dimensional space.

According to still another embodiment, a method of making a catheter according to the present invention includes the steps of providing an elongated body member and an ultrasound transducer, attaching the ultrasound transducer to the elongated body member, and forming an ultrasound dampening region adjacent to a portion of the ultrasound transducer. The ultrasound transducer is configured to transmit or to receive an ultrasound signal. The ultrasound dampening region is formed such that uniformity of the ultrasound signal is improved in three-dimensional space.

According to yet another embodiment, a method of making a catheter according to the present invention includes the steps of providing an elongated body member and a plurality of ultrasound transducers, attaching the plurality of ultrasound transducers to the elongated body member, forming a first ultrasound dampening region adjacent to a portion of at least one of the plurality of ultrasound transducers, and forming a second ultrasound dampening region between a sending one and a receiving one of the plurality of ultrasound transducers. The plurality of ultrasound transducers are configured to transmit and receive a plurality of ultrasound signals. The first ultrasound dampening region is formed such that uniformity of a corresponding communicated ultrasound signal is improved in three-dimensional space. The second ultrasound dampening region is formed to modify a conducted ultrasound signal conducted by the elongated body member to inhibit detection thereof.

According to still another embodiment, a catheter according to the present invention is made by one of the previous methods.

An object of the present invention is to improve the uniformity of an ultrasound signal in three-dimensional space.

A further object of the present invention is to reduce the conduction of ultrasound signals through the catheter between ultrasound transducers.

DETAILED DESCRIPTION OF THE PREFERRED EMBODIMENTS

Transducer assemblies according to the present invention may be mounted on various catheters. The catheter types can include reference catheters, marking/ablation catheters, mapping catheters, and linear lesion ablation catheters. To avoid duplication recognizable to one skilled in the art, when the following description discusses a specific type of catheter, discussion of all other types of catheters at the level of ordinary skill in the art is assumed.

Transducer assemblies according to the present invention may be employed with catheters used in an ultrasound tracking system. As used in this application, "transducer" refers to devices which are transmit-only, receive-only, or capable of both transmission and reception. A particular reference to a type of transducer, e.g., "transmitting transducer", means that the transducer is at least capable of transmission and may also be capable of reception. As used in this application, "communication" refers to transmission, reception, or both transmission and reception. As used in this application, "an emission" refers to radiation communicated by a transducer.

Returning to the ultrasound tracking system, such a system may include one or more reference catheters and an additional catheter. Each of the reference catheters carries one or more of the ultrasound transducers, with there being a total of at least four such transducers employed during use of the system. The reference catheter transducers can function as ultrasound receivers by converting acoustic pressure to voltage, and as ultrasound transmitters by converting voltage to acoustic pressure. At least four of the reference catheter transducers must be configured to receive and transmit ultrasound signals. The reference catheter transducers are used to generate the base coordinate system.

The additional catheter carries at least one ultrasound transducer which preferably functions as an ultrasound receiver but which may also function as a transmitter or a transmitter/receiver. The position of the additional catheter is displayed relative to the positions of the reference transducers.

Each transmitting reference transducer is separately made to emit acoustic pulses that are received by each of the receiving reference transducers so that the distances therebetween can be calculated using the respective time it takes for an acoustic pulse to travel between each pair of the reference transducers. These distances are triangulated to establish the positions of the reference transducers relative to each other, and therefore to establish a three-dimensional coordinate system. Such a tracking system is disclosed in copending application Ser. No. 08/905,090 filed Aug. 1, 1997, entitled "System for Electrode Localization Using Ultrasound", commonly owned by the assignee of the present application, the disclosure of which is incorporated herein by reference. The terms "tracking" and "localization" are used interchangeably in the copending application and the present application.

Preferably, the localization system is operated using the same vibration frequencies for all transducers. The optimal operating frequency for the system is determined by considering the resonant frequencies of the ultrasound transducers used for the catheters in the system. The resonant frequencies are determined by the size and shape of the transducer, for example, square or cylindrical.

Figures 7A, 7B:
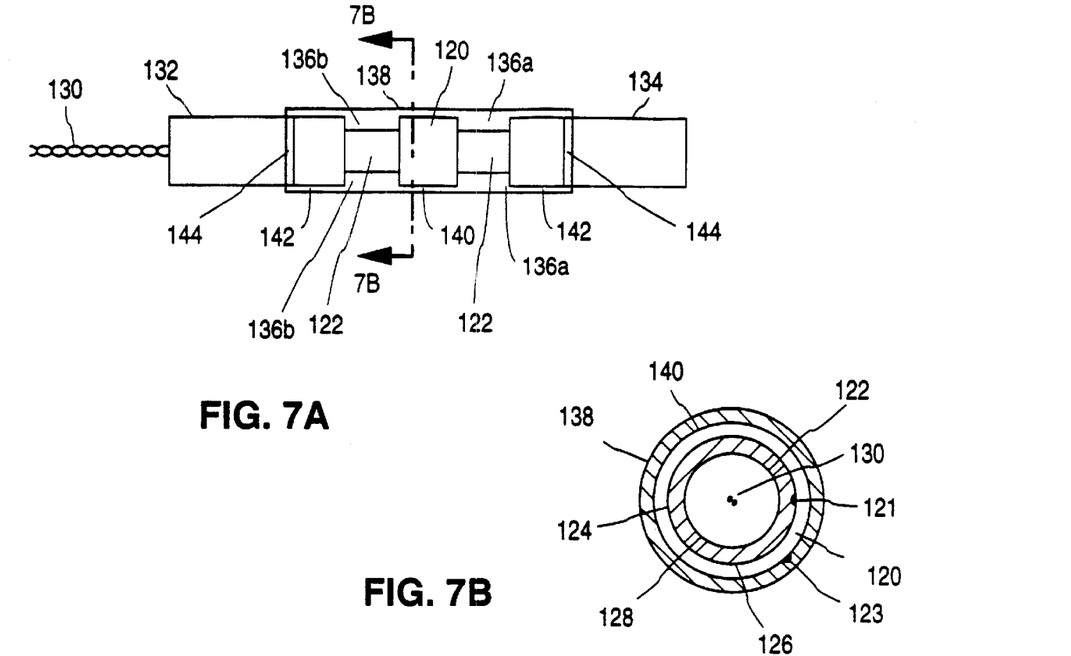
FIG. 7A is a cross-sectional view of a catheter according to the present invention taken on the longitudinal axis of the catheter.
FIG. 7B is a cross-sectional view taken on line 7B—7B of FIG. 7A.

FIGS. 7A and 7B show portions of a catheter 123 formed in accordance with the subject invention. A piezoelectric ceramic cylindrical transducer 120 is mounted on an inner shaft 122 of the catheter 123. An adhesive 124 can be used to bond the inner cylindrical electrode 126 of the transducer 120 and the outer surface 128 of the inner shaft 122 (see FIG. 7B). The interior of the inner shaft 122 contains electrical wires 130 for connection to the transducer 120 and other electrical devices attached to the catheter (see also FIG. 7B). The inner shaft 122 may be extruded from a flexible polymeric material such as a polyether polyamide copolymer. Wall thicknesses may be on the order of 0.005 inches.

Attached to each end of inner shaft 122 are outer shafts 132 and 134 which make up the body of the catheter. The outer shafts 132 and 134 also may be fabricated from a polyether polyamide copolymer or other polymeric material. The outer shafts 132 and 134 are attached to the inner shaft 122 by heat fusion or by the use of an epoxy material. In any case, the outer shafts 132 and 134 are brought up to approximately 0.020 inches from the end of the transducer 120, and any material to effect the joint preferably shall not be permitted in the gap between the outer shafts 132 and 134 and the transducer 120. This space defined by the end of the transducer 120, the end of the outer shaft 134, and a portion of the inner shaft 122 are ultrasound dampening regions 136a and 136b.

To keep air or vacuum in the ultrasound dampening region 136, a covering 138 may be pulled over and shrunk onto the transducer 120 and the ends of the outer shafts 132 and 134. The covering 138 may be a polymeric material, preferably polyethylene terepthalate (PET), and preferably with a wall thickness of less than 0.001 inches. To improve conduction of ultrasound from the transducer to the human body, a thin layer of adhesive 140 may be placed between the covering 138 and the transducer 120, such adhesive preferably not penetrating into the ultrasound dampening region 136 at the ends of the transducer 120. The covering 138 may be heat fused over the ends of the outer shafts 132 and 134. The covering 138 may also be adhered to the outer shafts 132 and 134 with adhesive 142. A sealant 144 may be used to help seal the air or vacuum within ultrasound dampening region 136.

Instead of being a tube of material placed over the transducer 120, the covering 138 may also be applied as a conformal coating. Areas desired to remain non-coated may be masked while the coating is applied, and then unmasked. The coating may be parylene applied in a vapor deposition process, or may be urethane applied by dipping. To prevent the coating from filling the ultrasound dampening region 136, the region is preferably filled with an ultrasound blocking material as discussed below.

The ultrasound dampening region 136 may be filled with an ultrasound blocking material that itself contains air. Such ultrasound blocking materials include highly scattering or absorbing materials such as highly loaded silicone rubber materials, composites of (typically shredded) lead loaded silicone rubber and epoxy, possibly glass microspheres in an epoxy matrix, foam, balsa wood, high-density polyethylene (HDPE) (such as that commercially available under the brand TYVEK), or expanded polytetrafluoroethylene (ePTFE). Most preferably, the ultrasound blocking material is ePTFE with a thickness of 0.020 inches.

The physical extent of the ultrasound dampening region at the end of the ceramic cylinders is dictated primarily by catheter assembly techniques. Even a small gap of less than 0.001 inches would be sufficient to prevent conduction of ultrasound from the end of the transducer 120. Bending of the catheter should not allow the outer shafts 132 and 134 to come in contact with the transducer 120. The covering 138 and sealant 144 should be sufficiently strong so as to not allow body fluids to penetrate into the ultrasound dampening region 136, and to provide additional protection against parts of the catheter breaking off and entering the body, such as if the transducer were to crack or shatter.

As shown in FIG. 7A, ultrasound dampening regions 136 are preferably located adjacent to the opposed end faces of cylindrical transducer 120. This attenuates the emission and reception from these surfaces. The cylindrical outer surface is not adjacent to one of the ultrasound dampening regions 136, allowing transmission of ultrasound from this surface. Reduction of the ultrasound communication associated with the end faces results in improved uniformity of the ultrasound signal in three-dimensional space.

Adhesives 124, 140, and 142 are preferably a penetrating epoxy material. An important property of adhesive 124 is that it flows into the interface between transducer 120 and inner shaft 122, preferably completely underneath transducer 120. This improves the mechanical grounding and the beam profile of transducer 120. Most preferably, the adhesive 124 is an epoxy such as "Epo-Tek 301".

A preferred transducer 120 is a piezoelectric cylindrical tube having inner and outer surfaces. The cylindrical transducer may be made of PZT-5H, PZT-5A, PMN (lead metaniobate or lead magnesium niobate) or other piezoelectric ceramic materials.

Electrodes 121 and 123 (see FIG. 7B) are positioned on the inner and outer surfaces of the transducer 120. The electrodes are metal surfaces not limited to materials such as sputtered chrome and gold, electroless nickel, or fired silver.

The piezoelectric ceramic is polarized in the thickness mode, i.e., between the two electrodes.

The cylinder includes an outside diameter of approximately 0.040 to 0.250 inches, and preferably approximately 0.060 to 0.090 inches. The cylinder has a length L of approximately 0.020 to 0.125 inches and preferably approximately 0.030 to 0.060 inches. Wall thickness W is approximately 0.004 to 0.030 inches and preferably approximately 0.006 inches to 0.015 inches.

Transducer 120 may alternatively be formed of piezoelectric polymer films of copolymers such as PVDF. Such films would have thicknesses of approximately 0.005–1.0 mm, and preferably approximately 0.007–0.100 mm, and would preferably include gold film electrodes on the inner and outer surfaces. The polymer film would be wrapped around inner shaft 122. A transducer configuration of this type operates with a very large band width and does not have a specific resonance due to the polymer piezoelectric.

Electrode leads 130 are attached to the inner and outer transducer electrodes 121 and 123. Preferably one of the leads is 42 gauge copper with a dielectric coating, and the other lead is 42 gauge silver with a dielectric coating. Most preferably, the dielectric coating on the electrical leads 130 is teflon. If piezoelectric ceramics are used, leads may be attached using low temperature solders which preferably contain large proportions of indium metal, or may be welded using a resistance welding process with a parallel gap. Leads 130 may alternatively be attached with silver epoxy. It is important that the leads be attached using a minimum amount of material to minimize distortion of the acoustic field. The physical mass of solder and wire are preferably kept to a minimum so as not to affect the acoustic performance of the device. The solder joints may cause local deformations of the inner shaft 122, outer shafts 132 and 134, or covering 138, in which case the adhesives 124, 140, and 142 will need to fill any voids caused by the perturbing joints.

In the case of the polymer transducers described above, photo lithographic techniques are typically used to create electrodes and their associated lead tabs. In this manner, the one side electroded polymer at the tab site does not contribute to the acoustic field. Leads are typically attached to these tabs with either low temperature indium based solders or with silver epoxy. Therefore, for these polymer transducers, the amount of material on the connection tab does not affect the acoustic field.

Figure 8:
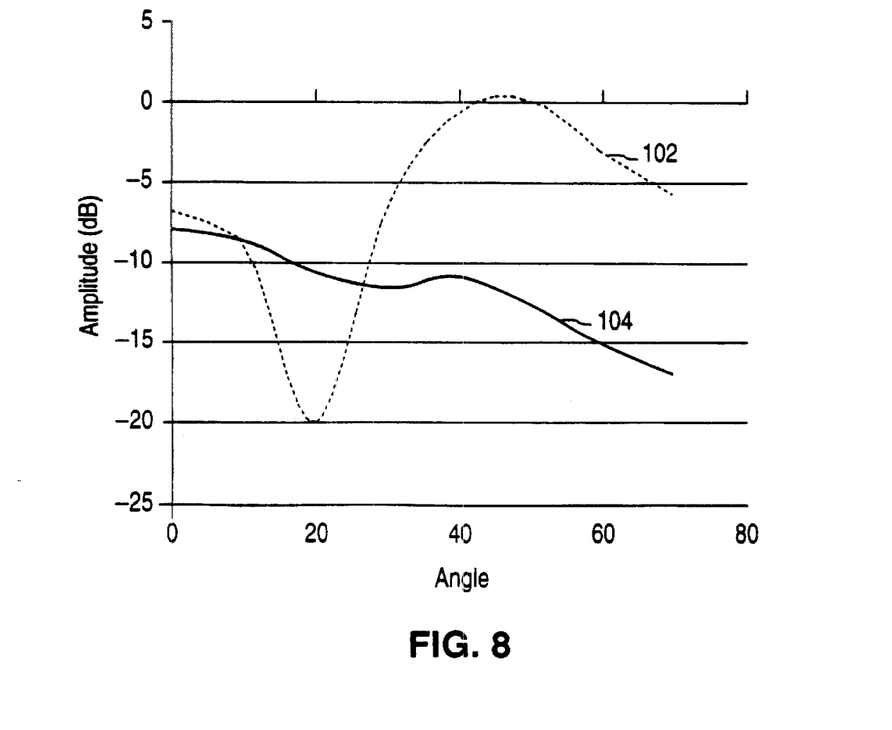
FIG. 8 is a graph of amplitude versus angle for two sets of transducers, one with an ultrasound dampening region and one without.

FIG. 8 shows the comparative performance of two sets of cylindrical transducers, one set with an ultrasound dampening region (containing air) and the other without. The transducers have an outside diameter of 0.090 inches, an inside diameter of 0.064 inches, and a length of 0.040 inches. The transmitting transducer in each set is driven with a single cycle sine wave at 1.5 MHz. The zero dB point is set at the largest received signal by either of the receiving transducers. All measurements are made at the same separation between transducers.

Waveform 102, without the ultrasound dampening region, has a wide variation in amplitude of about 20 dB over the measured angles. The destructive interference at about 20 degrees may attenuate a signal below the detection threshold, delaying detection of the pulse and resulting in a longer than actual distance measurement. The constructive interference at about 45 degrees may cause crosstalk from one transducer to another on the same catheter, resulting in earlier detection of the pulse and a shorter than actual distance measurement. Furthermore, any constructive interference at about 90 degrees will further contribute to ultrasound propagation down the catheter.

Waveform 104 results from a transducer formed with an ultrasound dampening region in accordance with the subject invention. As can be seen in this case, the amplitude variations range from about −7 dB to about −17 dB at about 70 degrees. This is much less variation than that of waveform 102, giving a signal with improved isotropy.

Figure 9:
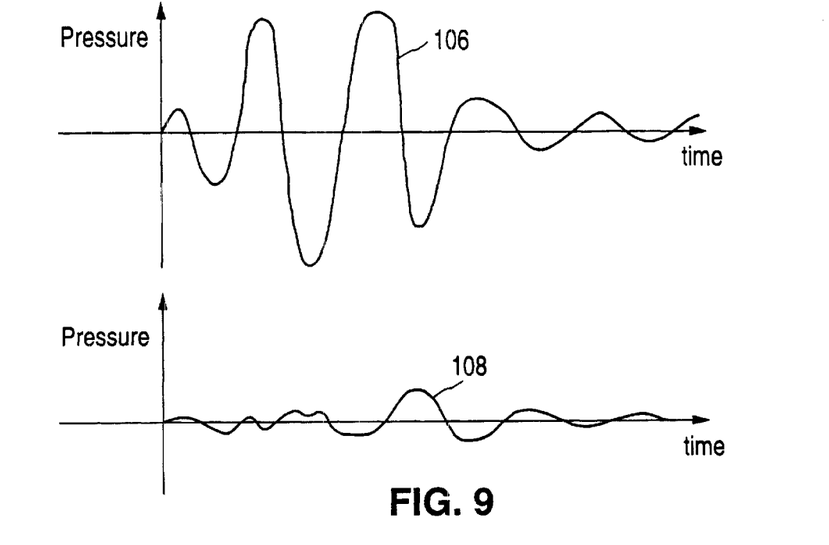
FIG. 9 is a graph of pressure versus time for the two sets of transducers measured in FIG. 8.

FIG. 9 shows the relative measured pressure as a function of time for the waveforms depicted in FIG. 8 at an angle of 20 degrees. The axes are scaled the same for both waveforms. The waveform 106 results from the set of transducers with the ultrasound dampening region, and the waveform 108 results from the set without. The first cycle of the waveform 106 is about the same magnitude as the largest cycle of the waveform 108. This implies varied detection times and correspondingly varied distance measurements.

Given the above description of the transducer assemblies according to the present invention, the following description provides preferred details concerning the catheters of which such transducer assemblies may be a part. In addition, although the above description of the invention has covered cylindrical and square transducers, the shape of the transducer is not relevant and similar principles may be applied to all other shapes of transducers.

Ultrasound Catheters

Figure 10:
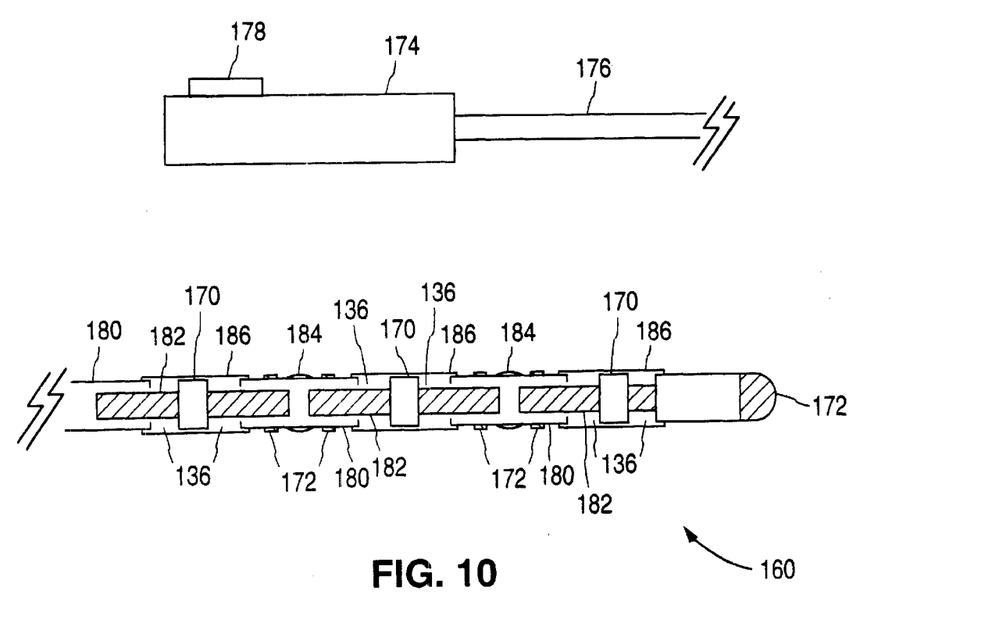
FIG. 10 is a cross-sectional view of a reference catheter according to the present invention taken on the longitudinal axis of the catheter.

Catheters of the type which may be used with the system according to the present invention are shown in FIGS. 10–11. These include a reference catheter 160 (see FIG. 10), a marking and ablation catheter, a basket-type mapping catheter 162 (FIG. 11), and a linear lesion ablation catheter.

Reference Catheters

Referring to FIG. 10, a reference catheter 160 according to the present invention is an elongate catheter having a plurality of ultrasound transducers 170 and a plurality of EP electrodes 172 positioned at its distal end, with one at its tip. The transducers 170 are piezoelectric transducers with ultrasound dampening regions as detailed above with respect to FIGS. 7A–7B. A handle 174 contains various electrical connectors and a deflection control 178 and provides maneuver control of the catheter 160. A shaft 176 connects the handle portion to the portion containing the transducers and the electrodes. The catheter preferably ends in an atraumatic tip that may also be one of the EP electrodes. Each transducer 170 configured to transmit is adjacent to ultrasound dampening regions 136 as described above.

The reference catheters can be integrated with typical EP catheters by providing the ultrasound transducers described above. This allows the tracking system to utilize the localization function using catheters which are already needed for the EP procedure. Thus, use of the tracking system does not require the physician to use more catheters than would be used had the EP procedure been carried out without the localization function.

For example, the reference catheter 160 may alternatively be an RV apex catheter having at least a distal pair of EP electrodes, an ultrasound transducer at the distal tip, and additional ultrasound transducers proximal to the distal tip. It may also be a coronary sinus reference catheter having at least three bipole pairs of EP electrodes distributed over the section of the catheter that is positioned in the coronary sinus, and having at least three ultrasound transducers also distributed over the section of the catheter that is in the coronary sinus. It may also be a high right atrial reference catheter having at least one bipolar pair of EP electrodes and at least three ultrasound transducers.

The reference catheter preferably includes at least four transducers. If desired, the reference catheter may have more transducers or it may have fewer transducers if more than one reference catheter is to be used to establish the three-dimensional coordinate system. Using more than four reference transducers total on all reference catheters is advantageous in that it adds redundancy to the system and thus enhances the accuracy of the system.

The transducers are spaced from one another along the catheter 160 by a distance of approximately 0.5–10 cm, and most preferably 1–3 cm.

Each transducer preferably has its own twisted pair wire attachment (see reference numeral 130 in FIG. 7A). When a transducer is to act as an ultrasound transmitter, a high voltage pulse (i.e., approximately 10 V-200 V peak-to-peak) is applied across the corresponding twisted pair and causes the transducer to generate an ultrasound pulse. When a transducer is to act as an ultrasound receiver, the ultrasound ranging hardware awaits receive pulses of approximately 0.01 mV–100 mV across the twisted pairs corresponding to receiving transducers. Additional leads (not shown) couple the EP electrodes 172 to hardware for amplifying cardiac signals (not shown).

To facilitate manipulation of the reference catheter through a patient's vessels and into the heart, the reference catheter may have a pre-shaped (e.g. curved) distal end. The reference catheter may also have a deflection control 178 on the handle 174 to pull a wire in the catheter and cause the distal end to curve. The handle 174 is preferably a polycarbon tube.

The shaft 176 is preferably a polyether polyamide copolymer braided shaft for its strength and torque response, and may also be formed using a braided polyamide, polyether, or copolymer. Preferably, the wire braid of shaft 176 is exposed at its end before shaft 176 is connected to the handle 174, and a conductive washer (not shown) is connected into the wire braid. This conductive washer can then be grounded by appropriate connection through the handle 174, thereby grounding the shaft 176 and reducing signal noise.

When a plurality of transducers 170 are located on a single catheter, ultrasound transmissions may be conducted by the catheter itself to a receiving transducer. If the conducted signal arrives before the signal transmitted through the bodily tissue, an erroneous distance calculation may be made. FIG. 10 illustrates numerous ways to reduce this conducted signal problem.

Most preferably, the inner shafts 182 may be placed in the outer shafts 180 such that adjacent inner shafts are not in direct contact with each other. Even though the inner shafts 182 are connected to the outer shafts 180, it has been found that a space between adjacent inner shafts reduces ultrasound conduction along the catheter. Alternatively, this space may be filled with an air loaded epoxy or other ultrasound blocking material as discussed above.

Second, the materials used to make the catheter may be selected to have an ultrasound conduction velocity less than that of the surrounding tissue. Ultrasound signals propagate in tissue at a speed of 1570–1580 m/sec. In such a situation, outer shafts 180 and inner shafts 182 may be made from a material with a slower conduction speed. For example, teflon has a conduction speed of about 1390 m/sec, and silicone has a conduction speed of about 1000 m/sec.

Third, the outer shafts 180 may have their own ultrasound dampening regions 184 located between transmitting and receiving transducers. Such regions 184 may be implemented in a manner analogous to that discussed above regarding ultrasound dampening regions 136 (see also FIG. 7A).

Fourth, coverings 186 (see reference numeral 138 in FIG. 7A) may individually cover each of the transducers 170, instead of using one covering for more than one transducer. This creates a gap between adjacent coverings. It has been found that the use of individual coverings reduces ultrasound conduction along the catheter.

Fifth, the ultrasound dampening region 136 (see FIG. 7A) may attenuate emissions and receptions from the end surfaces of the transducer, reducing ultrasound propagation along the catheter shaft, as explained with reference to FIG. 8 and the accompanying text.

Marking/Ablation Catheter

A marking/ablation catheter may be used to identify the locations of anatomical landmarks (such as the septal wall) relative to the coordinate system so that the landmarks may be included on the three-dimensional display. Showing anatomical landmarks on the display correlates the three-dimensional coordinate system to discrete anatomical locations and thereby assists the physician in navigating EP catheters to the desired locations within the heart.

The marking catheter is preferably a seven French steerable catheter having one or more ultrasound transducer(s) mounted at or near its distal tip. The catheter is steerable because it includes a deflection control and pull wire(s) that deflect the distal portion of the catheter. Preferably, the catheter includes one transducer at or near its distal tip and a second transducer spaced from the distal tip by approximately 0.5–4.0 cm. These two transducers indicate the direction of the distal portion of the catheter. A third transducer is spaced from the distal tip by approximately 3–10 cm. The third transducer enables determination of the direction in which the distal portion of the catheter is curved relative to the rest of the catheter. The marking catheter need not be one which is limited to use in marking anatomical sites. It can be a catheter useful for other purposes as well; the term "marking catheter" is being used in this description as a matter of convenience. The catheter may also include an ablation electrode at its distal tip, so that it may also be used to ablate tissue while the position of the ablation electrode is tracked using the localization system. It may also include other EP electrodes which may be used for pacing and/or tracking as desired by the user.

The transducers may be similar to the transducers 120 and may also include ultrasound dampening regions 136 (see FIG. 7A).

Alternatively, the more distal transducer might be packaged differently than the reference catheter transducers. For example, the transducer may be mounted just proximal of the distal ablation tip. Alternatively, a cylindrical transducer or a plate transducer may be positioned inside the distal ablation tip. An internal piezoelectric transducer would be embedded in a bead of epoxy 40 positioned in the catheter tip. This bead would preferably have a spherical contour across the distal end so that it would act as a divergent lens for the ultrasound energy. The metal forming the ablation tip should be very thin (i.e., less than a small fraction of a wavelength) to facilitate the transmission of acoustic energy to and from an internal transducer.

The marking catheter may additionally be provided with EP electrodes. As with the reference catheter 160 (see FIG. 10), a deflection control actuates a pull wire (not shown), allowing the marking catheter to be maneuvered through a patient's vessels and heart using conventional steering mechanisms. A connector enables the catheter to be electrically coupled to hardware and the ultrasound ranging hardware.

Mapping Catheter

Figure 11A:
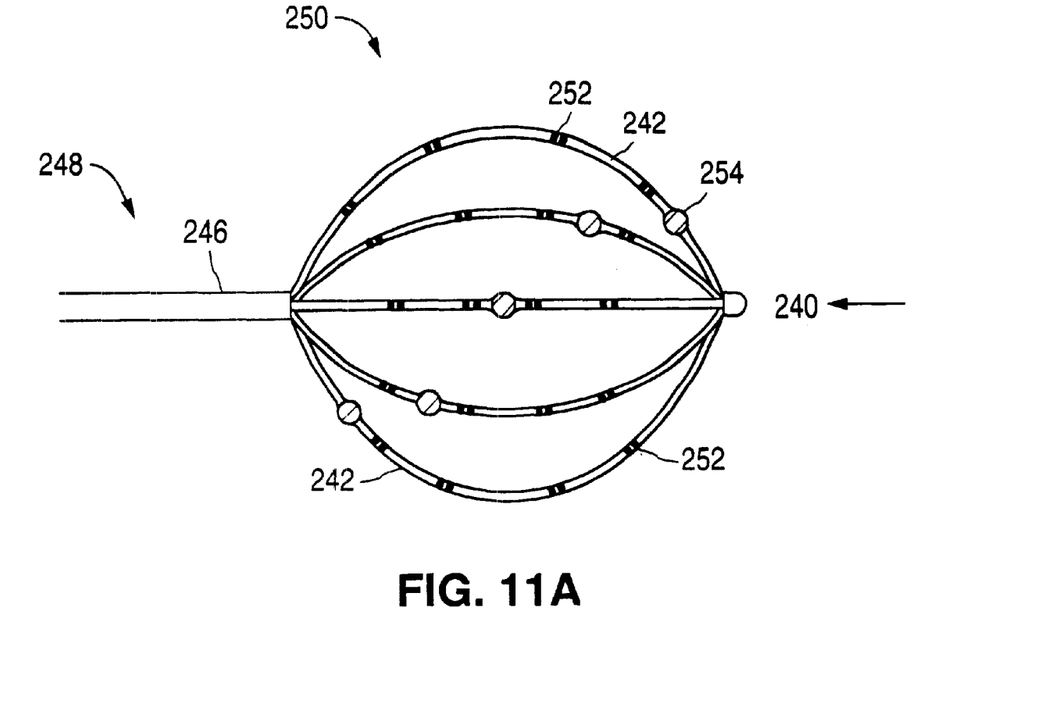
FIG. 11A is a perspective view of a basket catheter according to the present invention taken on the longitudinal axis of the catheter.
Figure 11B:
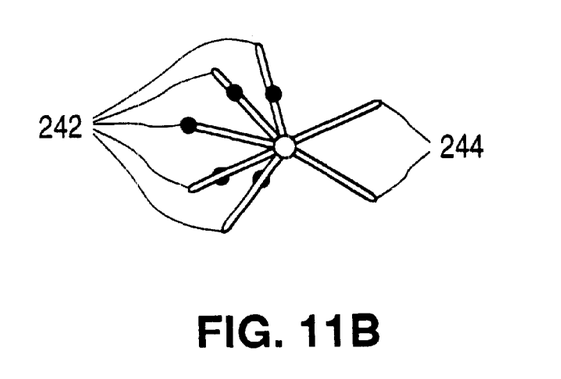
FIG. 11B is a perspective view of the catheter of FIG. 11A taken on the radial axis of the catheter.

FIGS. 11A and 11B show a preferred embodiment of a sector mapping catheter. FIG. 11B corresponds to a front view of FIG. 11A taken from the perspective of reference numeral 240. The five arms 242 may be concentrated at one section of the basket so that during use, measurements may be concentrated in one area of a cardiac chamber. The two arms 244 (see FIG. 11B) may be used for support. Examples of such mapping catheters, called sector mapping catheters, include those disclosed in U.S. Pat. Nos. 5,156,151, 5,425, 364, and 5,456,254, assigned to the assignee of the present application and incorporated herein by reference.

An outer sheath 246 of the catheter 248 is longitudinally slidable between a proximal position and a distal position in which the basket 250 is compressed within it. During use, the outer sheath 246 is first extended over the distal portion of the basket 250 to compress the arms. The catheter 248 can be inserted into the patient and moved, for example by a deflection control pull wire (not shown), through the patient's vessels and into the patient's heart. Once the distal end of the catheter 248 is within the desired chamber of the patient's heart, the outer sheath 246 is retracted, allowing the basket 250 to open into its expanded condition, either by spring action of the arms 242 or by a separate actuator. The electrodes 252 on the arms then come into contact with the chamber walls, permitting the electrical activity of the heart to be measured and mapped.

The transducers 254 are preferably cylindrical transducers with the arms 242 through their centers. The transducers 254 are preferably encapsulated within epoxy. The transducers may be staggered along the arms, as shown in FIG. 11A, to reduce the diameter of the basket 250 when the basket is in the compacted position to allow easier retraction into the outer sheath 246.

Figure 11C:
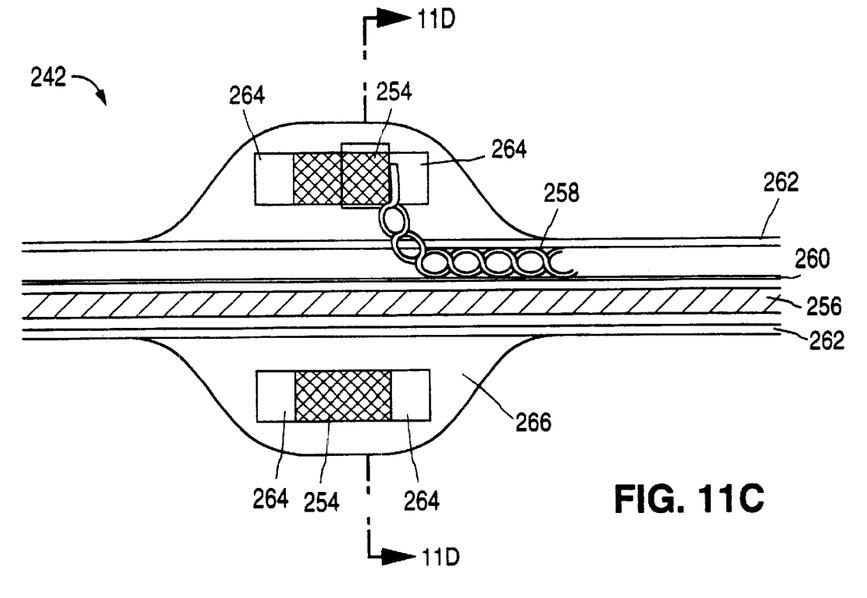
FIG. 11C is a cross-sectional view of one of the arms of the catheter of FIG. 11A taken along the long axis of the arm.
Figure 11D:
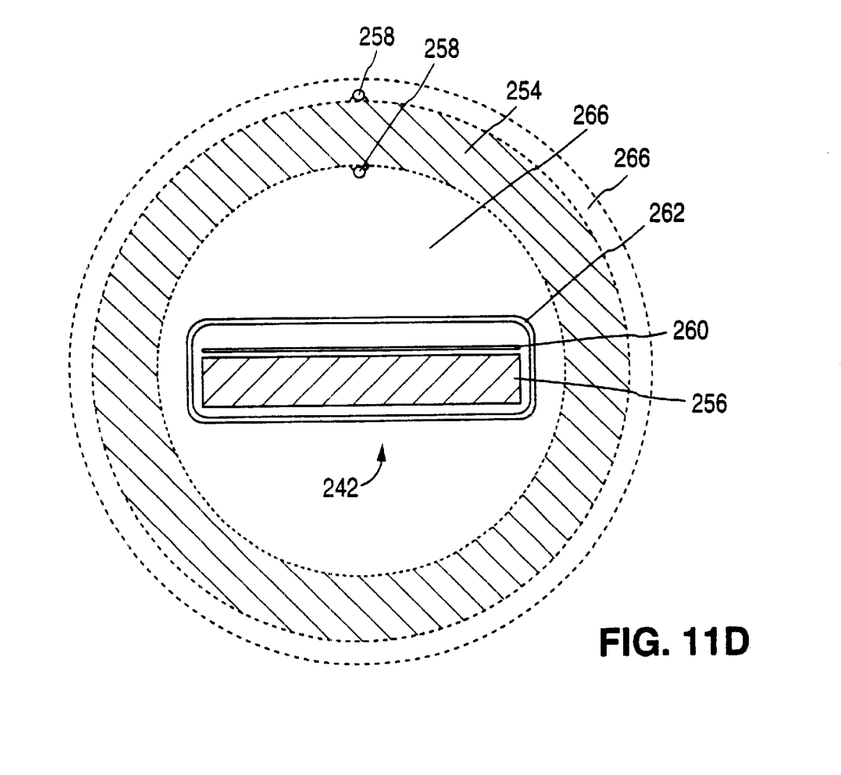
FIG. 11D is a cross-sectional view taken along line 11D—11D of FIG. 11C.

FIG. 11C shows a longitudinal cross-section of one of the arms 242. FIG. 11D shows a radial cross-section of one of the arms, taken along line 11D—11D in FIG. 11C. Shape memory material 256 provides the support structure for arm 242 and is preferably constructed of ribbons of Nitinol. The shape memory material 256 is treated such that the ribbons assume the expanded basket structure (see FIG. 11A) when in an unstressed condition.

If desired, twisted pair wires 258 electrically connects both an ultrasound transducer 254 and an EP electrode 252 to the tracking system. The twisted pair wires 258 therefore carries electrical activity measured by EP electrodes 252 as well as receive signals from the ultrasound transducers 254 to the tracking system. It is possible to do this because EP signals have a lower frequency (i.e., on the order of 1 Hz–3 kHz) than the ultrasonic signals, which have frequencies of approximately 500 kHz–30 MHz. Thus, the EP signals can be removed from the recorded signal using low-pass filtering while the ultrasound signal can be removed using high pass filtering.

Combining EP and ultrasound signals on the same twisted pair wires 258 has the advantage of reducing the total number of conductors in the catheter arm 242. While this is advantageous, it is not a requirement for functionality of the system. Naturally, the system may also be provided using separate leads for the EP and ultrasound signals.

Twisted pair wires 258 may be attached with low temperature solders which typically contain large proportions of indium metal or silver epoxy, or welded using a resistance welding process with a parallel gap. It is important that the leads be attached using a minimum amount of material to minimize distortion of the acoustic field. In the case of the polymer piezoelectrics, metallization of the electrodes and leads is typically achieved using photo lithographic techniques. In this manner, the one side electroded polymer at the lead site does not contribute to the acoustic field as discussed previously for the polymer transducer of the reference catheter.

The EP electrodes 252 are preferably platinum black electrodes having a size of approximately 0.009×0.030 inches. For these small electrodes, platinum black is used for low impedance, i.e., approximately less than 5.0 k Ohms over the frequency range (approximately 1 Hz–3 kHz) of interest for EP signals. This is important in that it prevents the impedance of the ultrasound transducers from loading the output of the EP electrodes.

There are many possibilities for the spacing of the bipole pairs of EP electrodes 252 and the transducers 254. The spacing of the transducers 254 may affect the positions of other structures on the basket, such as electrodes 252 and the arm junctions.

Printed wiring board 260 is preferably made using flex circuit technology. A flexible polymeric material provides support for thin conductive lines placed on the polymeric material of the printed wiring board 260.

Covering 262 covers shape memory material 256, printed wiring board 260 and twisted pair wires 258. Covering 262 is preferably PET shrink tubing, but may be any material as used for covering 138 (see FIG. 7A). The arm 242 may have a thickness of about 0.010 inches, and a width of about 0.040 inches.

Transducer 254 is cylindrical as mentioned above, and has a length of about 0.040 inches. Transducer 254 has an inner diameter of about 0.047 inches, and an outer diameter of about 0.067 inches. Given these dimensions, transducer 254 fits around arm 242.

Ultrasound dampening regions 264 are preferably located adjacent to the end surfaces of transducer 254. The ultrasound dampening regions 264 are similar to ultrasound dampening regions 136 as discussed above with reference to FIG. 7A.

Transducer 254 is preferably secured to the arm 242 by encapsulating epoxy 266. The epoxy 266 couples ultrasound energy to and from the outer and inner surfaces of transducer 254 with which it is in contact.

Figure 12:
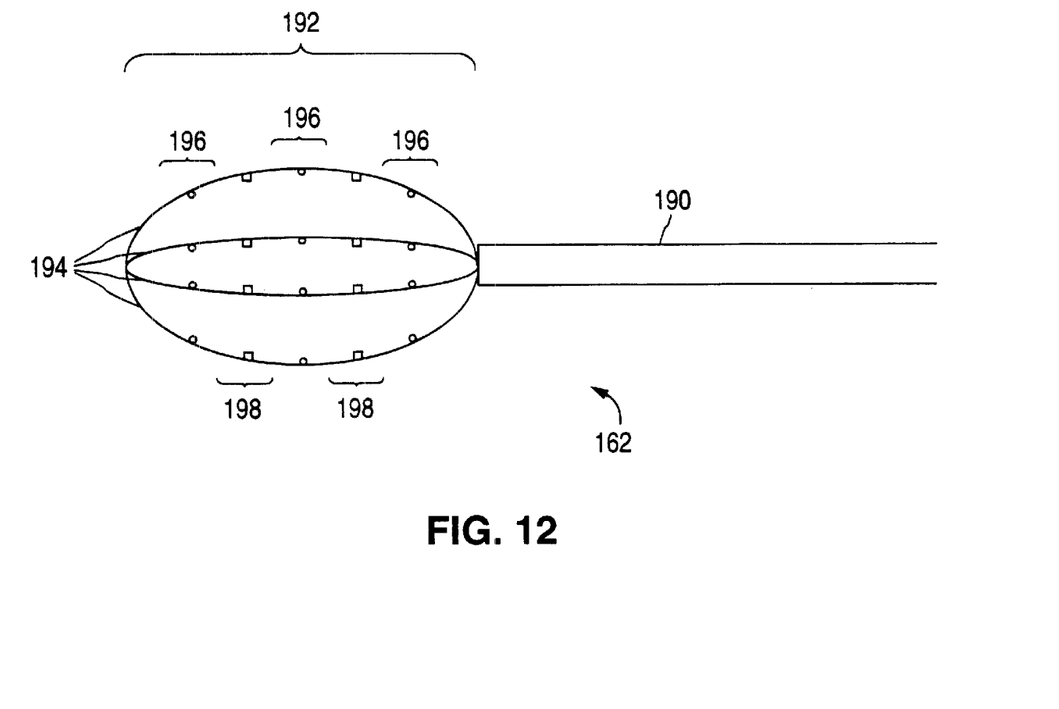
FIG. 12 is a perspective view of another basket catheter according to the present invention taken on the longitudinal axis of the catheter.

FIG. 12 shows another mapping catheter 162 including transducer assemblies according to the present invention. The catheter 162 is of the type known in the art as a "basket" or "array" catheter. It includes an elongate shaft 190 carrying a mapping basket 192 at its distal end. The basket 192 is formed of eight arms 194.

A plurality of ultrasound receiving transducers 198 are also mounted to each arm 194. The mapping electrodes 196 and the ultrasound transducers 198 may alternate with each other along the length of each arm 194, although there need not be one-to-one correspondence between the transducers and electrodes.

Figure 13A:
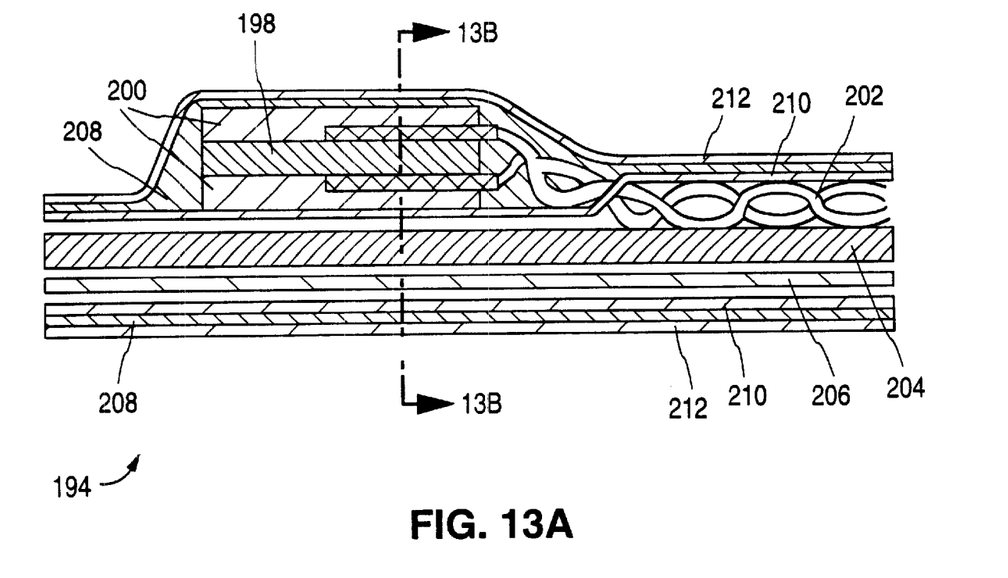
FIG. 13A is a cross-sectional view of an arm of the basket catheter of FIG. 11 taken along the long axis of the arm.
Figure 13B:
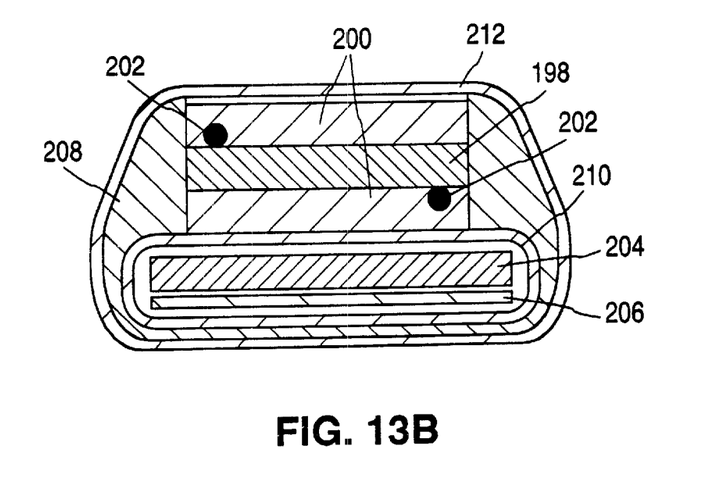
FIG. 13B is a cross-sectional view taken on line 13B—13B of FIG. 13A.

FIG. 13A is an expanded longitudinal cross-sectional view of one of the arms 194. FIG. 13B is a cross-sectional view along line 13B—13B in FIG. 13A. Shown are rectangular transducer 198, ultrasound dampening regions 200, twisted pair 202, shape memory material 204, printed wiring board 206, filling material 208, and coverings 210 and 212.

The transducer 198 may be as described above regarding transducer 120 (see FIG. 7A). Preferably, transducer 198 is a flat piezoelectric ceramic plate made of PZT-5H, PZT-5A, PMN (lead metaniobate or lead magnesium niobate) or other piezoelectric materials.

The transducer 198 includes a depth D and length L, each of approximately 0.010 to 0.060 inches, and preferably approximately 0.025 to 0.040 inches. The transducer has a wall thickness W of approximately 0.004 to 0.030 inches and preferably approximately 0.006 to 0.015 inches. The length and depth resonances of the transducer fall in the range from 1.0 MHz to 3 MHz and thus contribute to the overall performance of the system.

The transducers 198 may alternatively be formed of piezoelectric polymer films of copolymers such as PVDF. Such films would have thicknesses of approximately 0.005–1.0 mm, and preferably approximately 0.007–0.100 mm, and would preferably include gold film electrodes on the inner and outer surfaces. The polymer film would preferably be taped to the printed wiring board 206 of the basket arm, and leads attached to the top electrodes in a manner similar to that mentioned above for the reference catheter transducer. Alternatively, the polymer film could be used to form the entire flex circuit.

Twisted pair 202 may be similar to twisted pair 130 (see FIG. 7A) and similar to twisted pair wires 258 described above. Electrodes (not shown) are positioned on the upper and lower flat surfaces of the transducer 198. The electrodes are metal surfaces not limited to materials such as sputtered chrome and gold, electroless nickel, or fired silver. The piezoelectric ceramic is polarized in the thickness mode, i.e., between the two electrodes.

The EP electrodes 196 (see FIG. 12) are similar to EP electrodes 252 described above.

The ultrasound dampening regions 200 are along the top and bottom surfaces of transducer 198, dampening the emissions from these surfaces (as previously described). Preferably the ultrasound dampening regions 200 are made from high-density polyethylene such as the brand TYVEK with a thickness of approximately 0.002 to 0.040 inches, although the regions may be made as described above regarding ultrasound dampening regions 136 (see FIG. 7A).

As previously mentioned, acoustic wave propagation does not occur across a vacuum or air gap, consequently it may be desired to provide a conductive filler 208 to fill spaces around the sides of the transducer 198 between covering 210 and covering 212 to improve conduction of the ultrasound signal. Filler 208 may be made of silicone, rubber, or an insulating polymer.

Coverings 210 and 212 are preferably PET shrink tubing, but may be any material as used for covering 138 (see FIG. 7A).

Shape memory material 204 is preferably constructed of ribbons of Nitinol. The shape memory material is treated such that the ribbons assume the basket structure (see FIG. 12) when in an unstressed condition.

Printed wiring board 206 is preferably made using flex circuit technology. A flexible polymeric material provides support for thin conductive lines placed on the polymeric material.

Optionally, an ablation catheter lumen (not shown) may extend through the shaft 190 (see FIG. 12), which allows an ablation catheter to be introduced through the shaft 190 into contact with tissue surrounding the basket 192.

The shaft 190 (see FIG. 12) may also include a deflection lumen (not shown). A pull wire (not shown) may extend through the deflection lumen and facilitates steering of the basket using means that are conventional in the art.

Figure 14:
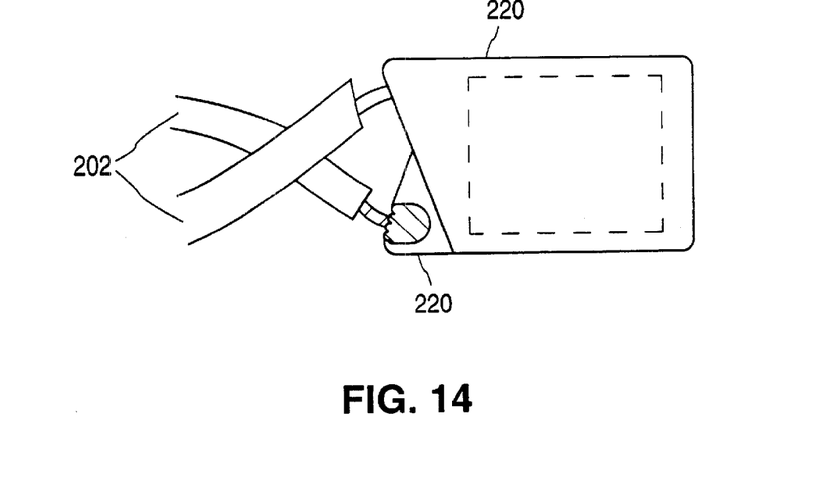
FIG. 14 is a plan view of a transducer shim according to the present invention.

FIG. 14 shows an alternative way of attaching the twisted pair 202 to the transducer 198 (not visible in this view). Metal shims 220 may be attached to the top and bottom of transducer 198. The shims 220 are preferably about 0.001 inches in thickness. The shims 220 are attached to the twisted pair 202 by a solder, preferably a low temperature solder which typically contains large proportions of indium metal.

Figure 15A:
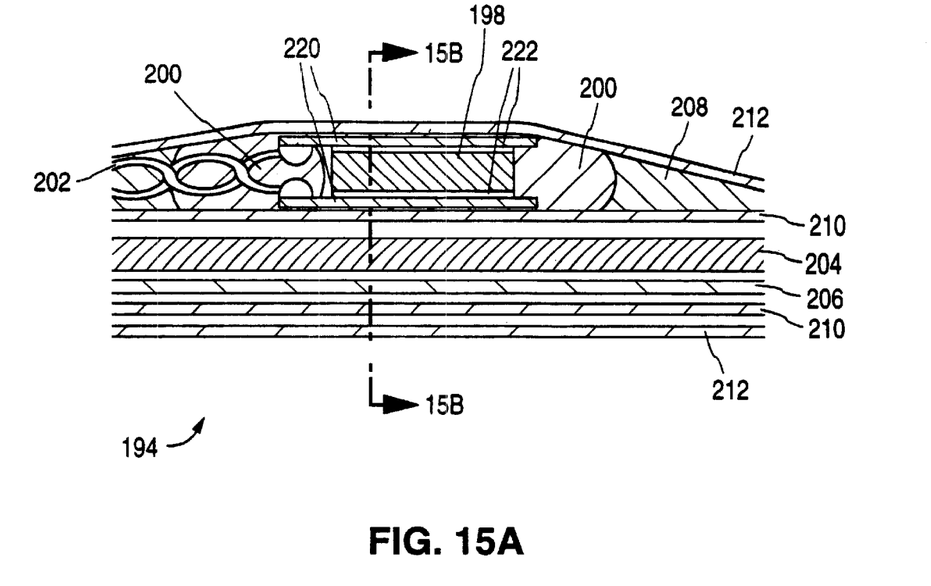
FIG. 15A is a cross-sectional view of an arm of the basket catheter of FIG. 12 taken along the long axis of the arm including the transducer shim of FIG. 14.
Figure 15B:
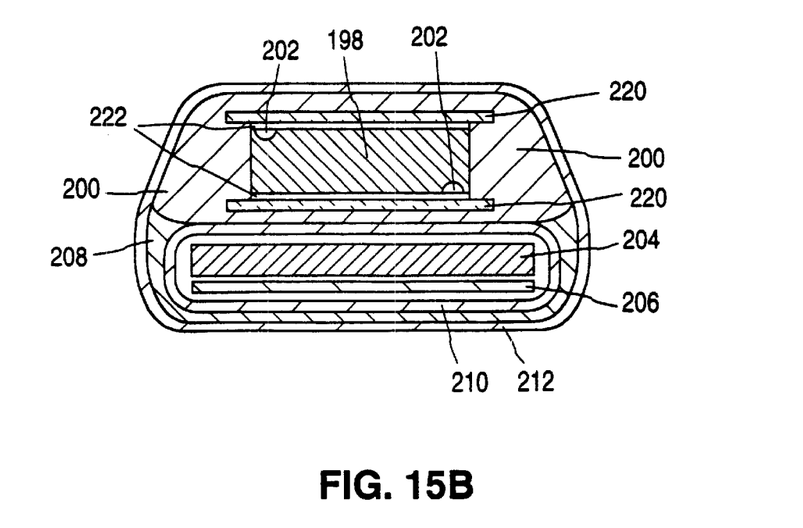
FIG. 15B is a cross-sectional view taken on line 15B—15B of FIG. 15A.

FIG. 15A shows that the alternative transducer 198 of FIG. 14 may be substituted into the arms 194 as shown in FIG. 13A, with the ultrasound dampening regions 200 located on the sides of transducer 198. FIG. 15B is a cross-sectional view along line 14B—14B in FIG. 15A. The shims 220 may be attached to the transducer 198 with a bonding agent 222 which may be a laminate, epoxy, or adhesive, such as "Epo-Tek 301" from Epoxy Technology, Billerica, Mass. For full performance of the ultrasound dampening region, none of the bonding agent 222 should be allowed to remain along the sides of transducer 198.

The like-numbered elements of FIGS. 15A–15B otherwise correspond as described above and are not further detailed.

Linear Lesion Ablation Catheter

A linear lesion ablation catheter generally resembles the marking/ablation catheter described above, with the addition of a plurality of RF ablation electrodes.

Other Ultrasound Transducer Applications

Figure 16A:
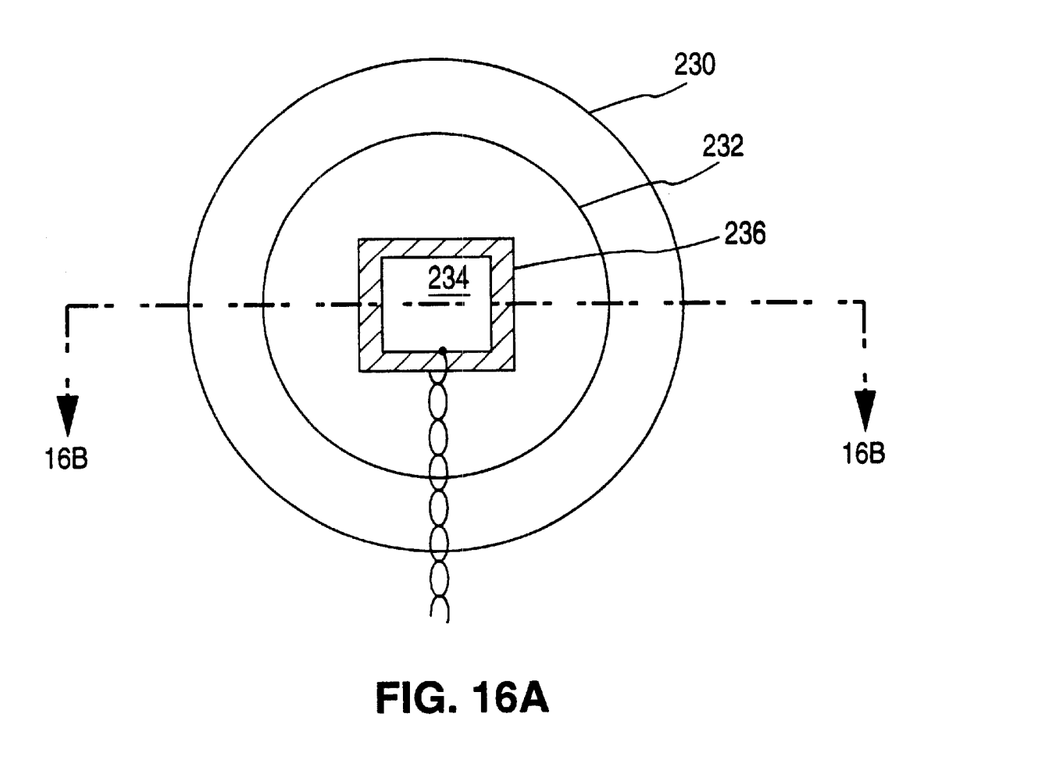
FIG. 16A is a plan view of another device including the transducer assembly of the present invention.
Figure 16B:
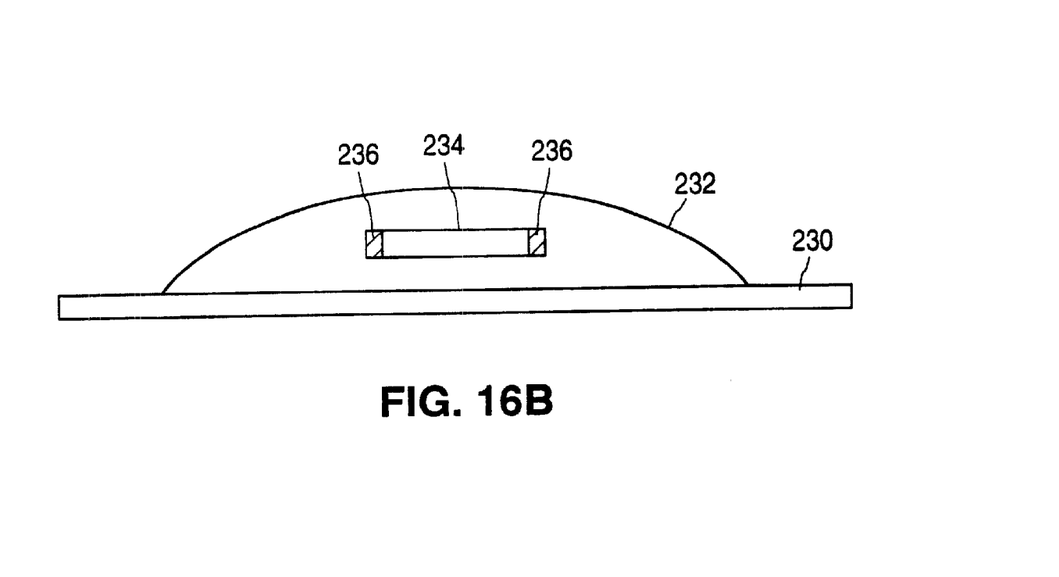
FIG. 16B is a cross-sectional view taken along line 16B—16B of FIG. 16A.

Although the discussion has focused on mounting the transducers on catheters for insertion into the body, other applications are possible. FIGS. 16A and 16B show a transducer assembly according to the present invention configured for external measurement. An adhesive patch 230 adheres the device to the outside of the body. Silicone or another gelatinous substance 232 covers the transducer 234 and the ultrasound dampening region 236. The silicone 232 communicates ultrasound between the transducer 234 and the body.

Although the ultrasound dampening region 236 is located adjacent to the side surfaces of transducer 234 in FIGS. 16A and 16B, other transducers and ultrasound dampening regions as discussed above may also be used.

It should be understood that various alternatives to the embodiments of the invention described herein may be employed in practicing the invention. It is intended that the following claims define the scope of the invention and that structures within the scope of these claims and their equivalents are covered thereby.

What is claimed is:

1. A method of making a catheter including an ultrasound transducer, said method comprising the steps of:

providing an elongated body member and an ultrasound transducer, wherein said ultrasound transducer is configured to transmit or to receive an ultrasound signal;

attaching said ultrasound transducer to said elongated body member;

forming an ultrasound dampening region adjacent to a portion of said ultrasound transducer, such that uniformity of communication of said ultrasound signal is improved in three-dimensional space.

2. The method of claim 1, wherein said ultrasound transducer is further configured to receive an ultrasound signal.

3. The method of claim 1, wherein said ultrasound transducer has a cylindrical shape including a radial outer surface and opposed end faces.

4. The method of claim 3, wherein said ultrasound dampening region is formed adjacent to said opposed end faces of said transducer.

5. The method of claim 1, wherein said ultrasound transducer has a rectangular shape including a top face, a bottom face, opposed width faces, and opposed length faces.

6. The method of claim 5, wherein said ultrasound dampening region is formed adjacent to said top face and said bottom face of said transducer.

7. The method of claim 5, wherein said ultrasound dampening region is formed adjacent to said opposed width faces of said transducer.

8. The method of claim 1, wherein said step of forming comprises:

providing a covering; and attaching said covering between portions of said elongated body member and said ultrasound transducer such that a space is defined, wherein said covering seals air within said space, said air defining an ultrasound dampening region such that uniformity of said ultrasound signal is improved in three-dimensional space.

9. The method of claim 8, wherein said covering comprises a tube polyethylene terepthalate.

10. The method of claim 8, wherein said covering comprises a conformal coating.

11. The method of claim 1, wherein said ultrasound dampening region includes a material selected from the group consisting of foam, balsa wood, high-density polyethylene, and expanded polytetrafluoroethylene.

12. A method of making a catheter including a plurality of ultrasound transducers, said method comprising the steps of:

providing an elongated body member and a plurality of ultrasound transducers, wherein said plurality of ultrasound transducers are configured to transmit and receive a plurality of ultrasound signals;

attaching said plurality of ultrasound transducers to said elongated body member;

forming a first ultrasound dampening region adjacent to a portion of at least one of said plurality of ultrasound transducers, such that uniformity of a corresponding communicated ultrasound signal is improved in three dimensional space; and forming a second ultrasound dampening region between a sending one and a receiving one of said plurality of ultrasound transducers to modify a conducted ultrasound signal conducted by said elongated body member to inhibit detection thereof.

13. The method of claim 12, wherein said plurality of ultrasound transducers each has a cylindrical shape including a radial outer surface and opposed end surfaces.

14. The method of claim 12, wherein said plurality of ultrasound transducers each has a cylindrical shape including a radial outer surface and opposed end faces.

15. The method of claim 12 wherein said plurality of ultrasound transducers each has a rectangular shape including a top face, a bottom face, opposed width faces, and opposed length faces.

16. The method of claim 15, wherein said first ultrasound dampening region is formed adjacent to said top face and said bottom face of said each transducer.

17. The method of claim 15, wherein said first ultrasound dampening region is formed adjacent to said opposed width faces of said each transducer.

18. The method of claim 12, wherein said step of forming a second ultrasound dampening region com rises providing a material having an ultrasound conduction speed of less than 1570 m/sec between a ending one and a receiving one of said plurality of ultrasound transducers.

19. The method of claim 12, wherein said step of forming a second ultrasound dampening region com rises forming a region containing one of air, a vacuum, and an ultrasound blocking material between a sending one and a receiving one of said plurality of ultrasound transducers.

20. The method of claim 12, wherein said step of forming a second ultrasound damping region comprises forming a space between ends of two inner shafts, and two inner shafts being connected to ends of an outer shaft, between a sending one and a receiving one of said plurality of ultrasound transducers.

21. The method of claim 12, wherein said step of forming a second ultrasound dampening region comprises:

providing a first covering and a second covering;

covering a sending one of said plurality of ultrasound transducers with said first covering; and covering a receiving one of said plurality of ultrasound transducers with said second covering such that a gap is formed between said first covering and said second covering.

22. The catheter made by the method of anyone of claims 1–21.

23. A method of making a catheter including an ultrasound transducer, said method comprising the steps of:

providing an elongated body member and an ultrasound transducer having a designed beamwidth, wherein said ultrasound transducer is configured to transmit or to receive an ultrasound signal;

attaching said ultrasound transducer to said elongated body member;

forming an ultrasound dampening region adjacent to a portion of said ultrasound transducer, such that uniformity of communication of said ultrasound signal within said beamwidth is improved in three-dimensional space.

24. The method of claim 23, wherein said ultrasound transducer is further configured to receive an ultrasound signal.

25. The method of claim 23, wherein said ultrasound transducer has a cylindrical shape including a radial outer surface and opposed end faces.

26. The method of claim 25, wherein said ultrasound dampening region is formed adjacent to said opposed end faces of said transducer.

27. The method of claim 23, wherein said ultrasound transducer has a rectangular shape including a top face, a bottom face, opposed width faces, and opposed length faces.

28. The method of claim 27, wherein said ultrasound dampening region is formed adjacent to said top face and said bottom face of said transducer.

29. The method of claim 27, wherein said ultrasound dampening region is formed adjacent to said opposed width faces of said transducer.

30. The method of claim 23, wherein said step of forming comprises:

providing a covering; and attaching said covering between portions of said elongated body member and said ultrasound transducer such that a space is defined, wherein said covering seals air without said space, said air defining an ultrasound dampening region such that uniformity of said ultrasound signal is improved in three-dimensional space.

31. The method of claim 30, wherein said covering comprises a tube of polyethylene terepthalate.

32. The method of claim 30, wherein said covering comprises a conformal coating.

33. The method of claim 23, wherein said ultrasound dampening region includes a material selected from the group consisting of foam, balsa wood, high-density polyethylene, and expanded polytetrafluoroethylene.

* * * * *